United States Patent [19]

Jost

[11] Patent Number: 4,473,552

[45] Date of Patent: Sep. 25, 1984

[54] ANAEROBIC METHOD FOR PRESERVING WHOLE BLOOD, TISSUE AND COMPONENTS CONTAINING LIVING MAMMALIAN CELLS

[76] Inventor: Leonora I. Jost, 401 E. 88th St., New York, N.Y. 10028

[21] Appl. No.: 403,939

[22] Filed: Aug. 2, 1982

Related U.S. Application Data

[63] Continuation-in-part of Ser. No. 244,137, Mar. 16, 1981, abandoned.

[51] Int. Cl.$^3$ .............................................. A61K 35/14
[52] U.S. Cl. ..................................... 424/101; 424/85; 424/95; 435/1; 435/2
[58] Field of Search ................. 435/2, 1; 424/101, 95, 424/85

[56] References Cited

PUBLICATIONS

Mizrahi et al.–Chem. Abst., vol. 73 (1970), p. 53686s.
Ganshirt–Modern Problems in Blood Preservation (1970), pp. 99–109.
Dorner et al.–Chem. Abst., vol. 84 (1976), p. 57012u.
Po et al.–Chem. Abst., vol. 95 (1981), p. 156,464b.

*Primary Examiner*—Sam Rosen

[57] ABSTRACT

An anaerobic method for preserving mammalian blood, mammalian tissue or living-cell containing components of either in a state of suspended animation, and the products of that method, are described. The method involves adding the substance to be preserved to a receptacle containing anticoagulant and low molecular weight hydroxyethyl starch, hydroxypropyl starch or polystarch containing from about 450 to about 1000 glucose units per molecule, mixing well, while maintaining the temperature in the range of from about 35° to about 40° F., and storing the resulting mixture at the same temperature. In a preferred embodiment which preserves blood, tissue or a component indefinitely, the structure is lightly crosslinked (i.e., about 1 cross-link per 50 g glucose units) with the aid of a water-soluble cross-linking agent of the acrylamide type, to form a gel structure.

When it is desired to use the preserved material, the swelled starch derivative may be liquefied, or the gel may be broken, by an isotonic wash or by microwaving. The bulk of the starch derivative and any acrylamide type crosslinker present are removed by filtration, whereupon the preserved material may be used in the same way as a freshly collected substance containing living cellular material might be used.

38 Claims, 3 Drawing Figures

ANAEROBIC METHOD FOR PRESERVING WHOLE BLOOD, TISSUE AND COMPONENTS CONTAINING LIVING MAMMALIAN CELLS

This application is a continuation-in-part of my application Ser. No. 244,137, filed Mar. 16, 1981, now abandoned.

The present invention relates to a method for preserving mammalian whole blood, mammalian tissue and various components of either which contain living mammalian cells, such as, e.g., the leukocyte or erythrocyte fraction of blood, a DNA fraction, a protein fraction, an immunoglobulin fraction, etc., and to preserved mammalian whole blood, tissue and components. According to the invention, the preserved whole blood, tissue or components remain in a suspended state, undeteriorated and usable to the same extent as fresh counterparts thereof would be. Effective preservation methods with similar results have long been sought without success. The most effective preservation and storage methods currently in use involve freezing and are in general effective only for the red blood cell ("RBC") or erythrocyte fraction of mammalian blood and then only to a limited degree. The method of the invention includes the use of an anaerobic system during processing and storing of the blood, tissue or components which precludes bacterial and fungal contamination from air, as well as oxidative changes and which suspends the normal metabolic processes of the living cells contained in the preserved substance during the storage period.

DESCRIPTION OF THE PRIOR ART

Most methods for long term preservation of mammalian whole blood, tissue or components thereof containing living cells require freezing, since the shelf life of these items under ordinary refrigeration is short. Whole blood, for example, cannot be maintained in usable condition for more than about 21 days under simple refrigeration. This is in part because the various cells continue to carry on their metabolic processes, eventually exhausting their nutrient supplies and deteriorating to such an extent that the blood will, after 21 days storage, contain 30% or more of nonviable cells which, if transfused to a patient, will promptly be removed from the patient's circulation as waste material. The freezing procedures currently in clinical use all involve glycerolizing the blood or, more usually, its erythrocyte fraction, freezing the glycerolized mixture, storing and then deglycerolizing after thawing but before use in transfusions and the like. See, e.g., Meryman, "Red Cell Freezing: A Major Factor of Blood Banks", included in *Clinical and Practical Aspects of the Use of Frozen Blood* (1977), a publication of the Committee on Workshops of the American Association of Blood Banks. Blood recovered from this method is subject to hazards of bacterial contamination during the deglycerolizing process and, to minimize this problem, current standards require the blood be used within 24 hours of deglycerolizing. In many patients, the residual glycerol in the transfused blood causes allergic reactions and other discomforts. Even when the preserved material is to be used for non-transfusion purposes—e.g., in the laboratory, the presence of residual glycerol and/or bacterial contamination occurring during deglycerolizing may cause problems.

Various preservation methods not in current clinical use have been suggested. In about 1952 when there was widespread concern about stockpiling blood platelets for in vivo use in case of atomic disaster, it was proposed to preserve the platelet fraction of whole human blood by gelling a mixture of platelets with a composition comprising of gelatin, sodium chloride, sodium acetate and glucose in the weight ratio of 0.3–1.2:0.36:0.08–0.20:2.0 and thereafter maintaining the gelled mixture at a temperature of about 4° C., (i.e., under ordinary refrigeration) as described in Tullis U.S. Pat. No. 2,786,014.

Another proposed method, described by Rinfret et al in U.S. Pat. No. 3,347,746, contemplated adding mannitol or a high molecular weight water soluble polymer such as polyvinyl pyrrolidone (PVP), dextran or albumin, in at least about 10% by weight, to the erythrocyte fraction of blood and then subjecting the mixture to a temperature below about $-100°$ C. until frozen. Ushakoff in U.S. Pat. No. 3,418,209 proposed a glycerolizing treatment involving replacement of at least 60% of the water normally present with glycerine, to render red blood cells stably storable at 4°–20° C. Knorpp in U.S. Pat. No. 3,758,382 taught that the freezing method of Rinfret et al produces a better preserved erythrocyte product if a hydroxyalkyl starch of molecular weight 40,000 to 70,000 and a degree of substitution from 0.5 to 1.0 is used in lieu of mannitol, PVP, dextran or albumin. Deindoerfer et al in U.S. Pat. No. 3,795,581 advocated treating red blood cells with 10 to 100 millimoles/liter of dihydroxyacetone and then storing at normal refrigerator temperature of about 1° to 6° C.

In U.S. Pat. No. 4,004,975, Lionetti et al. proposed a method for cryopreserving the leukocyte-containing granulocyte fraction of whole blood which employs hydroxyethylstarch (HES) as a combined cryoprotective and sedimenting agent and dimethylsulfoxide as a further cryoprotective agent, followed by freezing of the mixture. Lionetti et al point out (col. 3, ll. 14–27) that dextran, fibrinogen, gelatin, phytohemagglutinin and PVP have been suggested as cryoprotective agents but are not approved for human use—whereas HES is FDA-approved as both a cryoprotective agent and a sedimenting agent. Lionetti et al also point out that when white cells have been frozen with dimethylsulfoxide alone or with glycerol, a low yield of functional white cells is recovered after thawing. The method is said to be of special importance because preserved granulocytes are needed, e.g., to combat severe infections associated with severe granulocytopenia. It is also noted that as of 1975, when Lionetti et al. filed their application, nearly all of the leukocytes from millions of blood collections were wasted due to lack of an effective preservation method.

In contrast to Lionetti et al., Ridgway et al "Cryopreservation of Platelets Simplified; a Modified Glycerolglucose Method", *Transfusion*, Vol. 20, N. 4, pp. 427–431 (1980) taught that dimethylsulfoxide does act as a cryopreservative for platelets on an effective level but is less desirable than a glycerol-glucose cryoprotective agent because it evolves an objectionable odor on thawing and presents greater potential toxicity problems than the glucose-glycerol.

Dorner et al. in "Efficacy of Leucocyte-Poor Red Blood Cell Suspensions Prepared by Sedimentation in Hydroxyethyl Starch", *Transfusion*, Vol. 15, pp. 439–448 (1973) reported that high molecular weight HES, as a 6% solution in normal saline, can be used to promote sedimentation of leukocytes from red blood cells or whole blood. Because HES is an FDA-approved plasma volume expander, its use is preferred where the whole blood is to be used for transfusion of human patients with especially high sensitivity to leukocyte-carried antigens, so that efficient and safe leukocyte removal is of extreme importance. Several articles stress the cryo-protective efficacy of HES for frozen erythrocytes, including Allen et al. "Large Unit Red Cell Cryopreservation with Hydroxyethyl Starch", *Cryobiology* 13, 500–506 (1976), Allen et al. "Post-Thaw Suspension of Red Cells Cryopreserved with Hydroxyethyl Starch", *Cryobiology* 15, 375–381 (1978), Lionetti et al. "Improved Method for the Cryopreservation of Human Red Cells in Liquid Nitrogen with Hydroxyethyl Starch", *Cryobiology* 13, 489–499 (1976); Choudhury et al., "Freeze Preservation of Platelets using Hydroxyethyl Starch (HES); a Preliminary Report", *Cryobiology* 15, 493–501 (1978); Weatherbee et al., "Coagulation Studies after Transfusion of Hydroxyethyl Starch Protected Frozen Blood in Primates", Transfusion 14, pp. 109–115 (1974) and Allen et al., "Ultrastructure of Red Cells Frozen with Hydroxyethylstarch", Journal of Microscopy 117, pp. 381–394 (1979).

Ganshirt, "On the Influence of Different Additives in Blood Preservation" included in Modern Problems in Blood Preservation, edited by Spielmann et al. (1970) reports on experiments wherein erythrocytes were stored with each of gelatin, dextran, albumin and high molecular weight HES, and these compositions were compared for storage stability to an acid citrate dextrose (ACD)—whole blood mixture as control. Storage time was 5–8 weeks at 4° C. under anaerobic conditions. The author cautioned that all of the synthetic materials used contained traces of impurities which may have affected the results. His post-experiment conclusion was that there exists a need for confirmation of the results "by further investigations, including viability studies, before we try an interpretation and before they might have practical consequences".

Various letters to the editor of New England J. Med., 300, pp. 984–985 (1979) discuss the need for rendering whole blood, or red blood cells, storable at refrigerator temperatures for times in the order of at least 60 days.

The present invention provides a wide range of advantages over prior art methods of blood preservation. It is applicable to mammalian whole blood and also to mammalian tissue samples or any component of either that contains or comprises living cells. It therefore has the potential for satisfying many needs for living-cell containing components at less cost and in better condition than methods used heretofore. It utilizes a material, HES, which is nontoxic, safe and FDA-approved as a plasma extender. The method of the invention is inexpensive. Preserved blood, tissue, or components treated by the preferred method of this invention can be anaerobically stored under ordinary refrigerator conditions for an indefinite time and, because the metabolic processes of the preserved material are suspended during the period of preservation, the blood, tissue or living cell containing components is ultimately recovered in viable, usable form.

BRIEF DESCRIPTION OF THE INVENTION

The present invention, in its broadest compass, involves preserving whole blood, tissue, or any component of either, which contains living cells, usually in the presence of an anticoagulant, with an extracellular swelling agent consisting essentially of low molecular weight hydroxyethyl starch (HES), hydroxypropylstarch (HPS) or polystarch (PS). The starch structure may contain between about 450 and about 1000 repeating glucose units per molecule and preferably contains about 500 units. The temperature is maintained throughout at about 35° to about 40° F. and the ingredients are thoroughly mixed. In a preferred embodiment wherein the preserved product is to be stored for more than about sixty days, the starch derivative is swelled and cross-linked in situ in the presence of the material to be preserved providing in the order of about one crosslink per 20–50 glucose units. This is effected by reacting the starch derivative with a water-soluble cross-linking agent of the acrylamide type. Blood, tissue, or single components of either containing living cells, having been incorporated in this cross-linked HES, HPS or PS may be stored at about 35° to about 40° F., preferably 38° F., for an idenfinite period. It is essential that the swelling, gelation and storage of the substance to be preserved be effected under anaerobic conditions, preferably by purging the container with nitrogen and then excluding air thereafter.

When it is desired to use the preserved substance, the swelled starch derivative may be liquefied and/or the gel may be broken by microwaving or simple wash with an isotonic solution. Acrylamide-type-cross-linking agent, if present, and the preponderance of the starch derivative can be removed by simple filtration and the preserved blood, tissue or other living cell-containing component in essentially the same condition as at the time of collection or separation, is then ready for use.

Whole blood and RBC preserved according to the invention may be used in mammalian transfusions and for numerous other purposes. Blood and tissue components such as immunoglobulins, antibodies, antigens, antisera, leukocytes and leukocyte interferon, proteins, enzymes, etc. have a myriad of uses when preserved by the method of this invention. Tissue preserved in comminuted or particulate form, and finely divided blood-perfused tissue so preserved also have many uses.

BRIEF DESCRIPTION OF THE FIGURES

The FIGURES show a preferred type of receptacle for collection, treatment and storage of the material to be preserved.

DETAILED DESCRIPTION OF THE INVENTION

Figure 1:
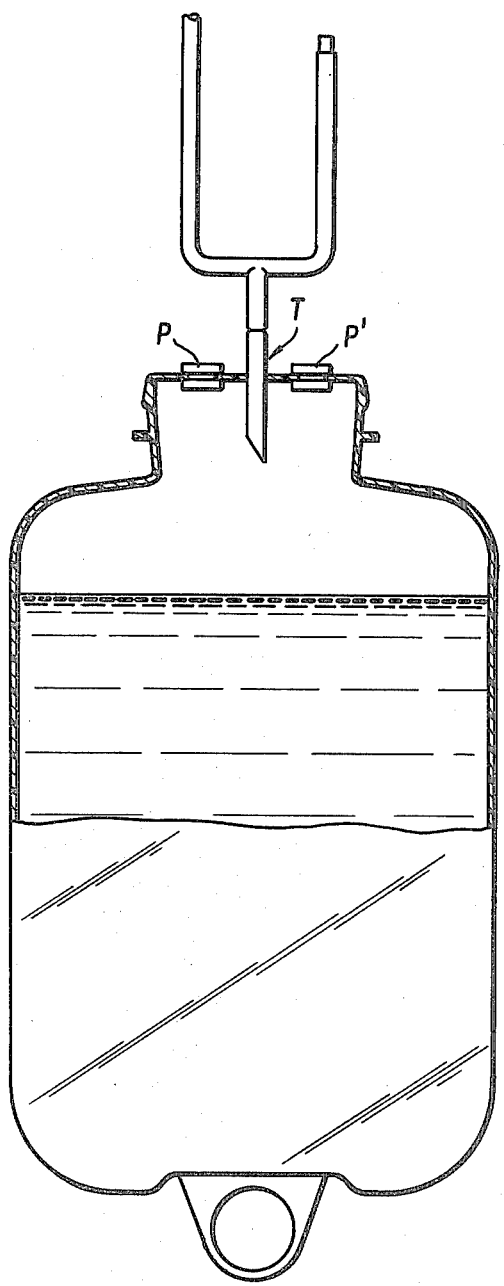
In FIG. 1, the receptacle is depicted as it appears during collection, e.g., of whole blood.

The method of the present invention may be used to preserve mammalian whole blood, mammalian tissue containing living cells or any living cell-containing component of either in a state of suspended animation. The method is simple and easy to use. It affords a practical and effective way, much needed in the art, for preserving living cellular material in a fresh undeteriorated state. It accordingly will greatly facilitate stockpiling of mammalian, including human, whole blood and fractions thereof. It affords a superior means of introducing to a mammalian subject, e.g., antisera, recombined DNA fragments, immunoglobulins, antibodies (both monoclonal and other antibodies), antigens, T-cells and like substances as to which the subject's own system is deficient. It affords an efficient mechanism of cleansing out undesired substances, e.g., unneeded and undesired antigens, carried by a particular subject's blood and then returning the cleansed blood to the subject. It particularly affords the possibility for removing, e.g., defective leukocytes or T-cells from a subject's own blood, substituting healthy counterpart cells and returning the treated blood to the subject with minimal disruption of the patient's autoimmune system and minimal introduction of foreign antigens which might trigger undesired allergic reactions.

The method of this invention thus offers great promise in the treatment of certain allergic, autoimmune and genetic diseases. In addition, it affords an enhanced opportunity to preserve blood and blood fractions which must now be discarded due to aging deterioration. In this regard, this invention affords the opportunity for routinely using preserved whole blood, rather than blood fractions, in transfusions, thus giving the promise of reduced patient shock and easier patient recovery than is sometimes experienced with, e.g., transfusion of thawed formerly frozen erythrocyte fractions.

The present invention also affords enhanced and improved means for in vitro testing of an individual mammalian patient's blood tissue under circumstances such that the cells (e.g., antigens, antibodies, T-cells, etc.) to be tested for, are maintained in a live state. In addition, it affords the promise of improved in vitro blood studies, both for general research purposes and for individual customized purposes designed to determine optimum treatment conditions and methods for particular patients having particular pathological problems. Thus, for example, whole blood, tissue or a specific component of either containing living cells, preserved according to the invention, may be subjected to gel fracture or starch derivative liquefaction, used as a culture medium for, e.g., a desired antigen, antibody, or recombined DNA molecule, returned to the suspended animation condition of the swelled and/or gelled state to facilitate certain types of desired study, the culture reactivated by further swell or gel fracture, etc. By carefully controlling the sequence of swelling or gelling and fracture steps and the periods of cell growth and metabolism, the clinician or researcher will be enabled to obtain in vitro data in undeteriorated natural mammalian media which simulate inter vivos conditions far more closely than the media now in use for such studies. The fact that interactions between recombined DNA molecules or monoclonal antibodies and their surrounding biological environment stops at room temperature is of particular assistance in planning controlled experiments with such entities wherein the techniques and products of this invention are also used.

The ingredients used in the method and products of this invention are simple and non-toxic. Where the material to be preserved is whole blood, a coagulatable blood fraction, a blood-perfused tissue sample or any other substance that is at least partly readily coagulatable, it is essential that an anticoagulant be admixed therewith promptly after collection from the mammalian donor. While the anticoagulant may be any effective anticoagulant known in the art, the preferred anticoagulant is acidified citrate-dextrose (ACD) which is added in the proportion (weight per volume) known in the art to be effective.

The preferred starch derivative to be utilized in the method and products of this invention is hydroxyethyl starch, because this material is known to be non-antigenic and non-toxic. It is also a Food and Drug Administration—approved plasma extender, swelling agent and cryopreservative. However, hydroxypropyl starch and polystarch are also effective and exhibit the same properties in the method and products of this invention as hydroxyethyl starch does.

It is critical to the invention that a narrow and low molecular weight fraction of starch derivative be utilized. This fraction must have at least about 450 glucose units per molecule and not more than about 1000 glucose units per molecule. In the preferred embodiments the number of glucose units per molecule is about 500. Among the many reasons for the criticality of the use of this narrow molecular weight fraction of starch derivative, not all of which are necessarily understood at present, are the necessity for easy and uniform miscibility with the material to be preserved, the desirability of achieving uniform swell in the mixture, and the need for easy miscibility with cross-linking agent when present. A preferred HES utilized in experimental work to date is a commercial HES of narrow and low molecular weight range available from Polyscience, Inc. As will be understood, any HES, HPS or PS having the critical characteristics will be operable in the method of the invention.

When the material to be preserved need be kept no more than 30-60 days, it is sufficient to use starch derivative alone as the preservative in this invention. For longer storage periods, the starch derivative should be swelled and lightly cross-linked to a gel, as hereinafter described. The weight of starch derivative per unit volume of material to be preserved may be varied within fairly wide limits depending upon the nature of the material to be preserved, the intended use of the preserved sample and when the mixture is to be gelled, the degree of swell that can be safely tolerated in the receptacle to be used for storage. A typical mix for preserving whole blood employs about 0.1 grams±0.02 grams of starch derivative per 100 ml of whole blood.

Thorough mixing of the starch derivative and, if present, the cross linking agent and anticoagulant, is extremely important to the successful practice of this invention. Uniform distribution of the protective agent comprising the starch derivative in the material to be preserved is essential. To that end, when the substance to be preserved comprises mammalian tissue it should first be comminuted by grinding if not already in particulate form. The uniform mixing is preferably achieved by a double centrifuging treatment, especially when whole blood or a blood fraction is to be preserved. Any other known method of thorough mixing, such as vortex mixing, or the like, may alternatively be used so long as the system is so maintained that extra air or oxygen is not added by the step.

In a preferred embodiment of the invention wherein whole blood or a blood fraction is to be preserved for an indefinite time, the proportions of starch derivative and cross-linking agent are selected so as to maintain the percentage of swell achieved in the mix at about 10%±1% by volume, but other proportions of swell may be preferred with other biological materials or for particular end use purposes.

It has been determined that under the temperature conditions employed pursuant to this invention, the maximum degree of swell is not attained until about 3 days after the ingredients are mixed. Gel set proceeds simultaneously with swell, commencing about 30 minutes after mixing and may also take up to about 3 days to be completed.

According to the invention, the temperature must be maintained at ordinary refrigerator conditions throughout mixing and storage, i.e., at a temperature in the range of from about 35° to about 40° F. Preferably a constant temperature of about 38° F. is maintained throughout.

In those instances where it is desired that the blood, tissue or component containing live cells be preserved for more than about 60 days, the starch derivative should be reacted in situ immediately after thorough admixture with the substance to be preserved, with an acrylamide-type cross-linking agent. The preferred cross-linking agent is one prepared by mixing tetramethylethylene diamine with ammonium or potassium persulfate, under sterile conditions, in acetone solution and then adding hydroxylysine, acrylamide or bisacrylamide dropwise. Hydroxylysine is a particularly preferred reactant. This mixture is allowed to stand under sterile conditions until it forms a reaction product which has the appearance of little worm-shaped fragments—a reaction which takes about 60 days to reach completion. These fragments are water-soluble. They have been found to effect random cross-linking of the starch derivative when thoroughly mixed therewith under the specified temperature conditions, to a cross-link density of about 1 crosslink for from about 20 to 50 glucose units and preferably about 1 crosslink for about 50 glucose units.

It has been observed that a specimen of the preferred cross-linking agent, which is worm-shaped and about one cm long takes about 30 minutes, at the temperature conditions specified, to thoroughly permeate the starch derivative mixture by diffusion.

It is believed that the gelation which is effected by the cross-linking agent is dependent upon ionic or electrical attractions and is a colloidal phenomenon, but applicant does not with to be bound by any particular theory in this regard. Other agents capable of swelling and lightly cross-linking the starch derivative to a gel may be alternatively used.

As has been noted, the composition, whether gelled or not, may be returned to its original fully liquid state by introduction of an isotonic solution, e.g., dilute aqueous NaCl or $MgCl_2$, or by imposing an electric field across the gel, e.g., by microwave device. Alternatively, the storage receptacle may be placed in a warm acetone-water bath. In all such instances, the mix should be brought to room temperature as rapidly as possible and filtered to remove most of the starch derivative and any amido cross-linking compounds that are present. The filtration should be conducted under sterile conditions and the preserved living cell-containing material constituting the filtrate should be used within no more than about 48 hours if it is to be replaced in a mammalian bodily environment. Any starch derivative remaining in the preserved living cell-containing substance will be metabolized by the mammal in its normal metabolic cycle.

While the upper limit of storage time during which living cell-containing substances can be preserved according to the preferred method of this invention has yet to be determined, whole blood gelled in accordance with this invention and stored anaerobically has been checked after 6 months by light scanning and laser meter counting of the live cells and has been found to be in the same state as when freshly drawn from the donor.

A critical parameter of the invention is that the processing and storage of the substance to be preserved must be conducted in an anaerobic atmosphere. This is achieved by purging the receptacle containing such substance with a gas inert to biological materials, mixing such substance with starch derivative while under a blanket of the same gas and storing the mix while still under this gas blanket.

The preferred gas for this purpose is nitrogen because it is more plentiful and less expensive than such inert gases as argon, xenon and krypton and it is inert, under the approximately 35° to 40° F. temperature conditions maintained in accordance with this invention, to biological substances containing living cells. Other inert gases may be substituted for nitrogen, however, without departing from this invention.

It is within the scope of the invention to substitute a proportion, in the order of up to about 25% by weight of the starch derivative, with a gellable animal protein such as gelatin. This particular embodiment is not preferred for preserving such products as whole blood or blood fractions intended to be used for transfusion pruposes because gelatin and the like are difficult to remove by washing or otherwise and it is believed that at least some patients might experience discomfort from its presence in the bloodstream.

Another disadvantage of this embodiment is that such proteins can not be swelled with acrylamide type cross-linkers as the starch derivatives can be. Since it is believed that the swelling of the starch derivative so as to embed and surround the substance to be preserved, thereby effectively insulating that substance even from the protective layer of nitrogen or other gas inert to such substance which surrounds the swelled or gelled mixture, is of particular importance in achieving an indefinite state of suspended animation of the living cells, the fact that the presence of gelatin diminishes the degree of swell is considered to be a disadvantage and imposes the limitation of about 25% by weight, based on starch derivative, upon the amount that may be used.

DESCRIPTION OF A PREFERRED EMBODIMENT

In a particularly preferred embodiment for use in the collection, preservation and storage of mammalian whole blood and blood derivatives, a special closed system receptacle, illustrated in the accompanying drawings, is used. This receptacle is illustrated in its preferred shape which is somewhat similar in plan view is narrower at its top, and wider at its bottom to accommodate the swell of the starch derivative during the preservation and storage steps. It is constructed of a sturdy, but collapsible material, preferably a flexible plastic of wall thickness in the order of about ⅛ to 1/16 inch, though any effective wall thickness will suffice. The plastic must be nonattackable by nitrogen or other inert gas and is nonreactive with and incapable of having any of its ingredients leached out by the mixture comprising starch and blood or blood fraction, even at room temperature or a slightly higher temperature. It is contemplated that any sturdy and suitably flexible, moldable plastic may be used for the receptacle if first given an interior sterile inert coating using methods and materials known in the art. The receptacle is equipped with a bottom loop so that is may be suspended from a hook, e.g. for transfusion purposes.

In the drawings, FIG. 1 illustrates a plan view of the receptacle in its preferred form. As shown, the receptacle is equipped with two one-way ports, P and P' which allow access to the receptacle but do not allow escape of any substance therefrom, each of which has an antigravity pick sealed into the cover. As depicted in FIG.

Figure 2:
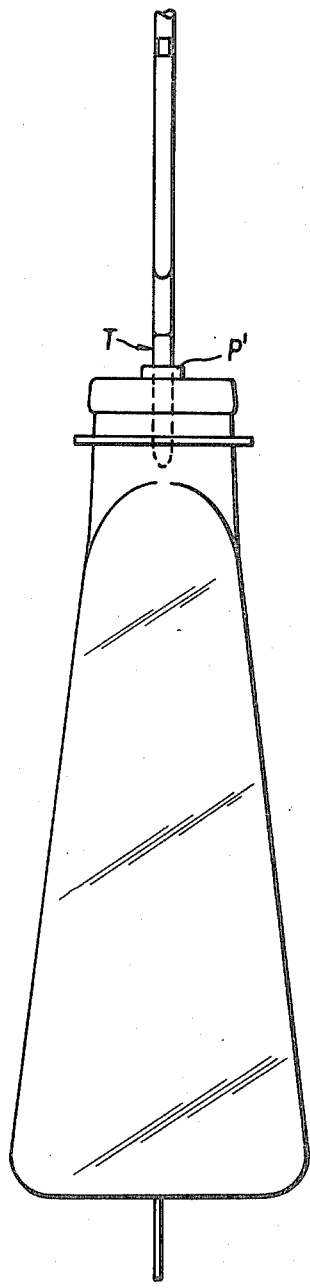
FIG. 2 shows a side view of the receptacle, including its preferred shape.
Figure 3:
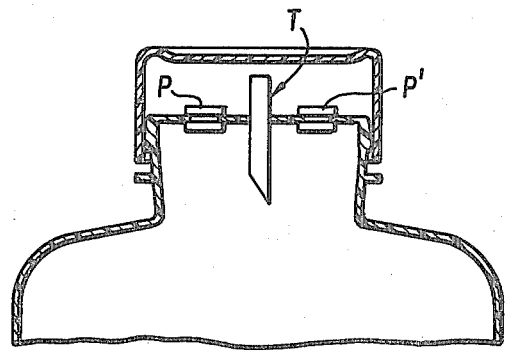
FIG. 3 depicts the receptacle with a loose cap over its valves, ready for storage.

1, the central two-way means of both access and egress, labelled T, is fitted with a U tube. It could equally as well be fitted with a "Y" blood recipient set, a straight blood recipient set, a special blood infusion set or with blood drip chamber accessories or any other form of conventional gravity blood collection set. FIG. 2 simply illustrates a side view of this receptacle, showing its preferred tapered shape, wider at the bottom than at the top. FIG. 3 shows the receptacle ready for storage and as stored, with T sealed off and a loose plastic cap fitted over the top. Alternatively this cap may be a snap-top mounted on a hinge or any other convenient form of cap.

When blood or one or more blood fractions are to be preserved according to this invention, the bottle is first partially filled with a solution in sterile water of anticoagulant and starch derivative. Where whole blood is to be stored, this solution contains 0.2 g anticoagulant, preferably ACD, and 0.1 g of starch drivative per 100 ml of sterile water. Thereafter, the whole blood is collected through the collection set which is attached at T, directly into the receptacle. The tube T is thereupon disconnected from the blood collection set and the receptacle is hooked up to a second one filled to the same level through a hookup pick sealed in the cover and a strut which is attached to it, and is centrifuged at about 4100 to about 7500 g for about 8–10 minutes, twice. The strut is removed, a pick is inserted into the already opened port of P and P' and the preferred cross-linking agent made by reacting tetramethylethylene diamine and hydroxylysine in the manner described above, in the form of a "worm" about 1 centimeter long for about each 500 ml of total mix, is added. The receptacle is then purged by attaching a valved needled tube connected to a nitrogen source to the one of P and P' which has previously been opened. Oxygen and air are allowed to escape through T. An oxygen sensor is utilized throughout to show the oxygen level in the receptacle. In a typical operation the nitrogen supply is attached to a power source, and the purge is accomplished, with power on, within a period of about 10–30 seconds during which the oxygen level in the receptacle drops, as shown by the oxygen sensor to no more than 1% by volume, preferably 0.5% or less, while the temperature in the receptacle concurrently is dropped to between about 35° and 40° F., preferably about 38° F. Swelling of the starch derivative becomes noticeable as the temperature lowering occurs. The receptacle is sealed at T; the opened port of P and P' automatically seals itself when the nitrogen pressure is removed. The container may then be stored at about 35°–40° F., preferably at 38° F. until needed.

When it is desired to separate freshly collected blood into a red cell and a white cell fraction and preserve both, the procedure is similar but the ligher white cell fraction containing leukocytes and plasma is poured out into a second bottle following the first centrifugation. In this case, cross-linking agent is separately added after both centrifugations to each of the receptacles containing the separated red and white cell fractions.

It will be understood that, within the scope of the invention, various methods may be used for separating crude components of either fraction in lieu of preserving both, and such crude components may be purified, e.g. for replication, and then stored in an appropriate receptacle with starch derivative and, if desired, cross-linking agent added before nitrogen purging and cooling. In many cases, these components will require the presence of various additives specific to preservation of their special functions, e.g., antibacterial agents, chain stoppers, etc.

The one port of P and P' on the receptacle which is not preforated during the filling, centrifuging, purging and cooling process is intended to be used when the receptacle is removed from storage, as an inlet port for oxygen and, if desired, isotonic solution such as saline. By introducing a filtration apparatus into the line at T, e.g., preserved whole blood on which the gel has been broken can be filtered and let directly into a transfusion set hooked up to a patient.

Having described the invention and various of its possible and preferred embodiments, it is not intended to limit it by the description given. Various alternative ways of proceeding in accordance with the invention and various embodiments not specifically described will be readily apparent to those skilled in the art, and it is intended that they be embraced within the scope of the invention, insofar as the appended claims may permit.

What is claimed is:

1. A stable, nondeteriorating article of manufacture comprising a sealed receptacle containing (1) a gas inert to the other contents thereof and (2) a composition of matter comprising (a) a biological substance containing mammalian living cells in a state of suspension and (b) a low molecular weight starch derivative selected from the group consisting of hydroxyethyl starch, hydroxypropyl starch and polystarch containing from about 450 to about 1000 glucose units per molecule, which article is maintained at a temperature of from about 35° F. to about 40° F.

2. An article of manufacture according to claim 1, wherein the biological substance comprises human whole blood and the starch derivative is hydroxyethyl starch.

3. An article of manufacture according to claim 1 wherein the biological substance comprises an erythrocyte fraction of mammalian whole blood and the starch derivative is hydroxyethyl starch.

4. An article of manufacture according to claim 1 wherein the biological substance comprises a leukocyte fraction of mammalian whole blood and the starch derivative is hydroxyethyl starch.

5. An article of manufacture according to claim 1 wherein the biological substance comprises a platelet fraction of mammalian whole blood and the starch derivative is hydroxyethyl starch.

6. An article of manufacture according to claim 1 wherein the biological substance comprises a plasma fraction of mammalian whole blood and the starch derivative is hydroxyethyl starch.

7. An article of manufacture according to claim 1 wherein the biological substance comprises an immunoglobulin fraction of mammalian whole blood and the starch derivative is hydroxyethyl starch.

8. An article of manufacture according to claim 1 wherein the biological substance comprises an antiserum fraction of mammalian whole blood and the starch derivative is hydroxyethyl starch.

9. An article of manufacture according to claim 1 wherein the biological substance comprises a purified component fraction of mammalian whole blood and the starch derivative is hydroxyethyl starch.

10. An article of manufacture according to claim 1 wherein the biological substance comprises particulate mammalian tissue and the starch derivative is hydroxyethyl starch.

11. An article of manufacture according to claim 1 wherein the biological substance comprises mammalian whole blood or a fraction thereof and the starch derivative is hydroxyethyl starch.

12. An article of manufacture according to claims 1, 2, 3, 4, 5, 6, 7, 8, 9 or 11 in which the composition of matter also contains an anticoagulant for mammalian blood.

13. An article of manufacture according to claims 1, 2, 3, 4, 5, 6, 7, 8, 9, 10 or 11 in which the composition of matter is swelled and gelled with a cross-linking agent.

14. An article of manufacture according to claims 1, 2, 3, 4, 5, 6, 7, 8, 9, 10 or 11 in which said gas is nitrogen gas.

15. An article of manufacture according to claim 1, 2, 3, 4, 5, 6, 7, 8, 9, 10 or 11 in which the composition of matter is swelled and gelled with a cross-linking agent and the cross-linking agent comprises a product formed by reacting tetramethylethylene diamine with acrylamide, bisacrylamide or hydroxylysine in the present of a water-soluble persulfate salt and allowing the mixture to stand for at least about sixty days.

16. An article of manufacture according to claims 1, 2, 3, 4, 5, 6, 7, 8, 9, 10 or 11 in which the composition of matter is swelled and gelled with a cross-linking agent and the cross-linking agent comprises a product formed by reacting tetramethylethylene diamine with hydroxylysine, acrylamide or bisacrylamide in the presence of a water-soluble persulfate salt and allowing the mixture to stand for at least about sixty days, and said gas is nitrogen gas.

17. An article of manufacture according to claim 15 in which the cross-linking agent comprises a product formed by reacting tetramethylethylene diamine with hydroxylysine.

18. An article of manufacture according to claim 16 in which the cross-linking agent comprises a product formed by reacting tetramethylethylene diamine with hydroxylysine.

19. An article of manufacture according to claim 12 in which the composition of matter is swelled and gelled with a cross-linking agent.

20. An article of manufacture according to claim 12 in which said gas is nitrogen gas.

21. A process for preserving a biological substance comprising living mammalian cells and rendering such composition storage stable at a temperature of from about 35° F. to about 40° F. which comprises the steps of,
adding to a suitable storage receptacle a sterile aqueous solution comprising a swellable, low-molecular weight starch derivative containing from about 450 to about 1000 glucose units per molecule and selected from the group consisting of hydroxyethyl starch, hydroxypropyl starch and polystarch,
adding to said sterile aqueous solution in said receptacle said biological substance comprising living mammalian cells,
thoroughly mixing,
purging said receptacle with a gas inert to the contents thereof while lowering the temperature to from about 35° F. to about 40° F.,
sealing the receptacle and storing it at a temperature of from about 35° F. to about 40° F.

22. The process of claim 21 wherein the biological substance comprises human whole blood and the starch derivative is hydroxyethyl starch.

23. The process of claim 21 wherein the biological substance comprises an erythrocyte fraction of human whole blood and the starch derivative is hydroxyethyl starch.

24. The process of claim 21 wherein the biological substance comprises a leukocyte fraction of human whole blood and the starch derivative is hydroxyethyl starch.

25. The process of claim 21 wherein the biological substance comprises a platelet fraction of human whole blood and the starch derivative is hydroxyethyl starch.

26. The process of claim 21 wherein the biological substance comprises a plasma fraction of human whole blood and the starch derivative is hydroxyethyl starch.

27. The process of claim 21 wherein the biological substance comprises an immunoglobulin fraction of human whole blood and the starch derivative is hydroxyethyl starch.

28. The process of claim 21 wherein the biological substance comprises an antiserum fraction of human whole blood and the starch derivative is hydroxyethyl starch.

29. The process of claim 21 wherein the biological substance comprises a purified component of human whole blood and the starch derivative is hydroxyethyl starch.

30. The process of claim 21 wherein the biological substance comprises particulate mammalian tissue and the starch derivative is hydroxyethyl starch.

31. The process of claim 21 wherein the biological substance comprises mammalian whole blood or a fraction thereof and the starch derivative is hydroxyethyl starch.

32. The process of claims 21, 22, 23, 24, 25, 26, 27, 29, 30 or 31 wherein the sterile aqueous solution also contains an anticoagulant for blood.

33. The process of claims 21, 22, 23, 24, 25, 26, 27, 28, 29, 30 or 31 wherein the said gas is nitrogen gas.

34. The process of claims 21, 22, 23, 24, 25, 26, 27, 28, 29, 30 or 31 wherein a cross-linking agent for said starch derivative is added after mixing and before purging.

35. The process of claims 21, 22, 23, 24, 25, 26, 27, 28, 29, 30 or 31 wherein a cross-linking agent for said starch derivative is added after mixing and before purging and the cross-linking agent comprises a product formed by reacting tetramethylethylene diamine with hydroxylysine, acrylamide or bisacrylamide in the presence of a water-soluble persulfate salt and allowing the mixture to stand for at least about sixty days.

36. The process of claims 21, 22, 23, 24, 25, 26, 27, 28, 29, 30 or 31 wherein a cross-linking agent for said starch derivative is added after mixing and before purging and the cross-linking agent comprises a product formed by reacting tetramethylethylene diamine with hydroxylysine, acrylamide or bisacrylamide in the presence of a water-soluble persulfate salt and allowing the mixture to stand for at least about sixty days, and said gas is nitrogen gas.

37. The process of claim 35 in which the cross-linking agent comprises a product formed by reacting tetramethylethylene diamine with hydroxylysine.

38. The process of claim 36 in which the cross-linking agent comprises a product formed by reacting tetramethylethylene diamine with hydroxylysine.

* * * * *